United States Patent
Perrin et al.

[11] Patent Number: 5,846,550
[45] Date of Patent: Dec. 8, 1998

[54] COMPOSITION IN THE FORM OF AN ANHYDROUS GEL WITH A WAX-FREE FATTY PHASE, CONTAINING AN ORGANOMODIFIED CLAY, EXPANDED THERMOPLASTIC HOLLOW PARTICLES AND A PYROGENOUS SILICA, AND ITS USES IN TOPICAL APPLICATION

[75] Inventors: Martine Perrin, Savigny sur Orge; Nadia Terren, Chevilly LaRue; Jacques Michelet, Champlan, all of France

[73] Assignee: L'Oreal, Paris, France

[21] Appl. No.: 652,687

[22] Filed: May 30, 1996

[30] Foreign Application Priority Data

May 30, 1995 [FR] France .................... 95 06387

[51] Int. Cl.$^6$ ........................................ A61K 7/26
[52] U.S. Cl. ................ 424/401; 424/63; 424/69; 424/486
[58] Field of Search ................. 424/401, 63, 59, 424/486; 252/89

[56] References Cited

U.S. PATENT DOCUMENTS

| | | | |
|---|---|---|---|
| 3,645,904 | 2/1972 | Beach | 252/89 |
| 4,431,673 | 2/1984 | Goldner et al. | 424/365 |
| 5,266,321 | 11/1993 | Shukuzaki et al. | 424/401 |
| 5,475,661 | 12/1995 | Pillai et al. | 424/401 |

FOREIGN PATENT DOCUMENTS

| | | |
|---|---|---|
| 2486800 | 7/1980 | France . |
| 0605284 | 12/1993 | France . |
| 1372701 | 1/1972 | United Kingdom . |

Primary Examiner—Thurman K. Page
Assistant Examiner—D. Faulkner
Attorney, Agent, or Firm—Finnegan, Henders, Farabow, Garrett & Dunner, L.L.P.

[57] ABSTRACT

A composition in the form of an anhydrous gel containing a wax-free fatty phase in which are dispersed an organomodified clay, expanded thermoplastic hollow particles of polymer or copolymer formed from a monomer or a mixture of monomers containing ethylenic unsaturation and a pyrogenous silica, as well as to its uses in topical application.

This composition has a creamy, non-greasy, smooth and melting texture and good stability over time.

It may be used as a base for make-up products or care products for the skin and/or the face. It may contain heat-sensitive cosmetic or dermatological active agents.

45 Claims, No Drawings

COMPOSITION IN THE FORM OF AN ANHYDROUS GEL WITH A WAX-FREE FATTY PHASE, CONTAINING AN ORGANOMODIFIED CLAY, EXPANDED THERMOPLASTIC HOLLOW PARTICLES AND A PYROGENOUS SILICA, AND ITS USES IN TOPICAL APPLICATION

The present invention relates to a composition in the form of an anhydrous gel with a wax-free fatty phase, described below, and containing an organomodified clay, expanded thermoplastic hollow particles and pyrogenous silica, as well as to its uses in topical application, in particular in cosmetics and/or in dermatology.

Make-up compositions containing a fatty phase are commonly used in cosmetics because of their good adhesion to the epidermis, their pleasant feel, their protective capacity and their capacity to form a waterproof film. Anhydrous make-up products are generally in a compact solid form or alternatively in the form of a cream.

Compositions having a creamy consistency are more sought after insofar as they may be applied in a satisfactory manner with the fingers from packaging in the form of a jar or a tube. They generally contain waxes so as to maintain a stable consistency over time. These wax-based products are obtained by melting the waxes at high temperatures, generally above 80° C., so as to be able to integrate them homogeneously in their formulation. It proves to be impossible to incorporate heat-sensitive cosmetic or dermatological active agents into compositions of this type.

In the industry, it has thus been sought to produce wax-free greasy make-up products which may be manufactured at room temperature so as to be able to incorporate heat-sensitive active agents, and products whose texture is sufficiently creamy to allow satisfactory spreading with the fingers. However, in the absence of wax, a lack of stability of these products may be expected over time, caused by phenomena of softening or of release of oil leading to a greasy and sticky texture as well as difficulty in spreading.

Applicants have discovered, surprisingly, that the use of the combination of an organomodified clay and thermoplastic hollow particles of expanded polymer or copolymer formed from a monomer or a mixture of monomers containing ethylenic unsaturation and pyrogenous silica, dispersed in a fatty phase containing essentially no wax, and preferably, no wax, led to compositions in the form of anhydrous gels which were stable over time and had a homogeneous, non-greasy, smooth, non-sticky, melting texture which was sufficiently creamy to be spread in a satisfactory manner with the fingers.

These compositions may be prepared by simple mixing and homogenization at room temperature and may thus contain heat-sensitive active agents.

A composition in accordance with the invention in the form of an anhydrous gel comprises:

(a) a fatty phase containing essentially no wax;
(b) an organomodified clay;
(c) expanded thermoplastic hollow particles of polymer or of copolymer formed from a monomer or from a mixture of monomers containing ethylenic unsaturation; and
(d) a pyrogenous silica.

The phrase "essentially no wax" is defined herein to mean that the composition of the invention can contain some wax but cannot contain an amount of wax that would preclude manufacture of the composition at room temperature and would also preclude a texture of the composition that does not allow satisfactory spreading with the fingers.

Preferably, 1% or less wax relative to the total weight of the composition is employed in the compositions of the invention. More preferably, "essentially no wax" means 0.5% or less, relative to the total weight of the composition, and most preferably 0%.

The fatty phase constituting the base of the composition of the invention preferably represents from 60 to 85% by weight and more particularly from 65 to 77% by weight of the total weight of the composition.

The fatty phase comprises at least one oil chosen from:

oils of mineral, plant or animal origin, such as liquid petrolatum, soya oil, sunflower oil, sesame oil, rapeseed oil, sweet almond oil, macadamia oil, blackcurrant pip oil, karite butter and the liquid fraction thereof and perhydrosqualene;

synthetic oils such as fatty acid esters or fatty alcohols such as, for example: parleam, isostearyl neopentanoate, isopropyl myristate, isopropyl stearate, 2-ethylhexyl palmitate, isopropyl lanolate, isononyl isononanoate, isotridecyl isononanoate, octyl palmitate, oleyl alcohol, saturated fatty acid triglycerides of plant origin such as caprylic/capric acid triglycerides, for instance those sold by the company Stearineries Dubois or those sold under the names Miglyol 810, 812 and 818 by the company Dynamit Nobel, and hydrogenated polyisobutene;

silicone oils such as cyclomethicones such as, for example, cyclopentadimethylsiloxane and cyclohexadimethylsiloxane; and polydimethylsiloxanes;

phenylated or hydroxylated silicone gums;

fluoro oils; and mixtures thereof.

The organomodified clays are preferably chosen from the products of reaction of a hectorite or of a montmorillonite and a quaternary ammonium salt, in particular stearyldimethylbenzylammonium chloride or the quaternary ammonium chloride of the formula:

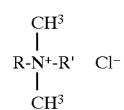

in which R and R' represent a mixture of alkyl residues having from 14 to 20 carbon atoms derived from hydrogenated tallow.

According to the invention, the organomodified clays are preferably present at concentrations preferably ranging from 0.5 to 6% by weight of active material and more particularly from 2 to 5% by weight relative to the total weight of the composition.

Hectorites or montmorillonites organomodified in the form of gels comprising the said organomodified clay, an oil of mineral, plant, animal or synthetic origin such as those defined above and a wetting agent such as propylene carbonate are used more particularly.

Examples which may be mentioned are the products sold under the names Miglyol Gel B, Miglyol Gel T, Miglyol 840 Gel B and Miglyol 840 Gel T by the company Dynamit Nobel. These products contain a hectorite or a montmorillonite modified with a stearyldimethylbenzylammonium chloride salt, a mixture of capric and caprylic acid triglycerides and propylene carbonate.

The particles which may be used according to the invention may be prepared from monomers containing ethylenic unsaturation, which are non-toxic and non-irritant to the skin. The particles of the invention may be obtained, for example, according to the processes of patents and patent applications EP-056,219, EP-348,372, EP-486,080, EP-320, 473, EP-112,807 and U.S. Pat No. 3,615,972, the disclosures of which are incorporated by reference herein.

In general, the internal cavity of the particles contains a gas which may be air, nitrogen or a hydrocarbon such as isobutane or isopentane.

Among the monomers used to produce the expanded thermoplastic hollow particles of the invention, mention may be made of methacrylic or acrylic acid esters such as methyl acrylate or methacrylate; vinylidene chloride; acrylonitrile; styrene and derivatives thereof; butadiene and derivatives thereof; and mixtures thereof.

It is possible, for example, to use the polymers or copolymers of methyl acrylate or methacrylate, the copolymers formed from styrene and acrylonitrile, and the copolymers of vinylidene chloride and acrylonitrile or vinyl chloride.

Use is preferably made of a polymer or a copolymer containing: from 0% to 60% of vinylidene chloride or one of the derivatives thereof, from 20% to 90% of acrylonitrile or one of the derivatives thereof and from 0% to 50% of a (meth)acrylic or styrene monomer, the sum of the percentages (by weight) being equal to 100. The (meth)acrylic monomer is, for example, methyl or ethyl (meth)acrylate. The styrene monomer is, for example, styrene or α-methylstyrene.

More preferably, the particles used in the present invention are hollow particles of an expanded copolymer of vinylidene chloride and acrylonitrile or of vinylidene chloride, acrylonitrile and methyl methacrylate. These particles may be dry or hydrated.

Advantageously, the particles of the invention have a particle size ranging from 1 µm to 100 µm and, even better, ranging from 5 µm to 60 µm, and better still from 10 µm to 50 µm.

The density of the particles is preferably chosen within the range from 15 kg/m³ to 200 kg/m³ and, even better, from 40 kg/m³ to 120 kg/m³ and better still from 60 kg/m³ to 80 kg/m³.

The particles which may be used in the invention are, for example, microspheres of expanded terpolymer of vinylidene chloride, acrylonitrile and methacrylate, sold under the brand name Expancel by the company Nobel Casco under the references 551 DE 50 (particle size of about 40 µm), 551 DE 20 (particle size of about 30 µm and density of about 65 kg/m³), 551 DE 12 (particle size of about 12 µm), 551 DE 80 (particle size of about 80 µm) and 416 DE 50 (particle size of about 50 µm). It is also possible to use microspheres formed of the same expanded terpolymer having a particle size of about 18 µm and a density of about 70 kg/m³, referred to below as EL 23.

The expanded thermoplastic hollow particles in accordance with the invention are present in concentrations preferably ranging from 0.1 to 3% by weight and, more particularly, from 0.5 to 2% by weight relative to the weight of the composition.

The pyrogenous silica present in the compositions of the invention may be in the form of hydrophilic or hydrophobic pyrogenous silica. The pyrogenous silicas can be obtained by high-temperature hydrolysis of a volatile silicon compound in an oxyhydrogen flame. This results in the production of a finely divided silica. The surface may be chemically modified by reduction of silanol groups, for example with a dimethylsiloxane or a trimethylsiloxane, so as to obtain a hydrophobic silica.

The products sold under the names Aerosils 200, R 972 and R 974 by the company Degussa are used in particular.

The pyrogenous silica is present in the compositions of the invention at concentrations preferably ranging from 0.1 to 3% by weight relative to the total weight of the composition.

A particularly preferred form of composition according to the invention also contains a silicone gel comprising a partially crosslinked organopolysiloxane of three-dimensional structure included in a silicone oil of low viscosity. The addition of this silicone gel allows the softness and melting qualities of the compositions of the invention to be improved.

Preferred silicone gels used according to the invention are characterized in that they comprise:

(a) a partially crosslinked polyorganosiloxane of three-dimensional structure chosen from:

(i) polyorganopolysiloxanes comprising units of $R_2SiO$ and $RSiO_{1.5}$ and optionally units of $R_3SiO_{0.5}$ and $SiO_2$ or $SiO_2$ in which the radicals R, independently of each other, denote a hydrogen, an alkyl such as methyl, ethyl or propyl, an aryl such as phenyl or tolyl and an unsaturated aliphatic group such as vinyl and in which the weight ratio of the units of $R_2SiO$ to the units of $RSiO_{1.5}$ ranges from 1/1 to 30/1;

ii) insoluble polyorganopolysiloxanes different from the polyorganopolysiloxanes (i), the insoluble polyorganopolysiloxanes being swellable in silicone oil, and being obtained by addition of an organohydrogenopolysiloxane (1) and an organopolysiloxane (2) having unsaturated aliphatic groups, such that the amount of hydrogen or of unsaturated aliphatic groups in (1) and (ii) respectively ranges from 1 to 20 mol % when the organopolysiloxane is non-cyclic and from 1 to 50 mol % when the organopolysiloxane is cyclic; and (b) a silicone oil of viscosity less than or equal to 0.5 Pa s; the partially crosslinked polyorganosiloxane/silicone oil weight ratio ranging from 5/95 to 30/70.

The silicone oils of low viscosity are chosen, for example, from a linear methylphenylpolysiloxane or dimethylpolysiloxane with a low degree of polymerization, an octamethylcyclotetrasiloxane, a decamethylcyclopentasiloxane or a mixture of octamethylcyclotetrasiloxane and decamethylcyclopentasiloxane.

The silicone gels used according to the invention are known and are described in U.S. Pat. No. 5,266,321, the disclosure of which is incorporated by reference herein. They are prepared according to the processes defined in this same document.

The product sold under the name KSG16 by the company Shin Etsu is used in particular. This product contains a mixture comprising a linear polydimethylsiloxane of low viscosity (0.06 Pa s) and a partially crosslinked polydimethylsiloxane of three-dimensional structure.

The partially crosslinked polyorganosiloxanes are present in the compositions of the invention at active material concentrations preferably ranging up to about 8% by weight relative to the total weight of the composition.

The compositions according to the invention may be in the form of foundations or tinted creams and may contain inorganic or organic pigments.

Among the organic pigments which may be mentioned are lakes such as the calcium lakes of D and C Red No. 7, the barium lakes of D and C Red No. 6 and 9, the aluminium lakes of D and C Red No. 3 and of D and C Yellow No. 5 and the zirconium lakes of D and C Orange No. 5. Among the inorganic pigments which may be mentioned are: iron oxides (red, brown, black and yellow), chromium oxides, ultramarines (aluminosilicate polysulphides), titanium dioxide, manganese pyrophosphate and Prussian blue (ferric ferrocyanate).

The pigments are present in concentrations ranging preferably from 0 to 20% by weight and more particularly from 3 to 12% by weight relative to the total weight of the composition.

The compositions according to the invention may also contain agents such as, for example, magnesium carbonate, starch or modified starches, polyethylene powder, zinc powder, zinc oxide, magnesium stearate or zinc stearate, microbeads of silicone resin such as the product sold under the name Tospearl by the company Toshiba, and silica microspheres, to obtain a matte-effect. They are present in concentrations ranging preferably from 2 to 15% by weight and more particularly from 5 to 10% by weight relative to the total weight of the composition.

The compositions according to the invention may also contain cosmetic or dermatological active agents such as vitamin A, vitamin E, vitamin A palmitate and vitamin F and additives such as preserving agents, fragrances, sunscreens, antioxidants, bactericides, moisturizing agents, melanin and fillers such as talc, kaolin, mica and nanotitaniums.

Another subject of the invention comprises cosmetic and/or dermatological compositions, characterized in that they comprise compositions as defined above.

The compositions according to the invention may be used as bases for make-up products such as foundations, complexion enhancers, make-up correctors, tinted creams or eyeshadows or alternatively as bases for care products for the skin and/or the face such as, for example, white creams for smoothing out the relief around the eyes.

They are preferably packaged in tubes or jars and are applied easily with the fingers onto the skin and/or the face.

Guided by the teachings in this specification, a person skilled in the art can routinely choose possible additional compounds and/or the amounts thereof so that the advantageous properties intrinsically associated with the combination in accordance with the invention are not damaged, or are substantially not damaged, by the addition(s) envisaged.

The examples which follow serve to illustrate the invention without, however, being limiting in nature.

EXAMPLE 1

Foundation

| | |
|---|---|
| Hectorite modified with stearyldimethylammonium chloride in gel form (Miglyol GeI B from Dynamit Nobel) | 30.0% |
| Expanded particles of vinylidene chloride/acrylonitrile/methacrylate copolymer enclosing isobutane (Expancel 550 DE 20 from Nobel Casco) | 1.5% |
| Hydrophobic pyrogenous silica surface-modified with trimethylsiloxane (Aerosil R 972 from Degussa) | 1.0% |
| Silicone gel comprising a mixture of polydimethylsiloxane (0.06 Pa s)/crosslinked polydimethylsiloxane (75/25) sold under the name KSG16 by Shin Etsu | 15.0% |
| Pigments | 12.0% |
| Sunscreen | 4.0% |
| Talc | 8.0% |
| Fragrance | 0.3% |
| cyclopentadimethylsiloxane | 19.5% |
| Isostearyl neopentanoate | 8.7% |

The composition was prepared as follows:

The process was performed at room temperature. The pigments were dispersed in the volatile silicone oil. The gel based on modified hectorite and the silicone gel were added with stirring. The pyrogenous silica was added and the mixture was homogenized. The fragrance, the active agents and the hollow expanded particles, which were impasted beforehand in the isostearyl neopentanoate, were next incorporated. The talc was next introduced. Finally, the dispersion was made fine by grinding.

EXAMPLE 2

Complexion Enhancer

| | |
|---|---|
| Hectorite modified with stearyldimethylammonium chloride in gel form sold under the name Miglyol GeI B from Dynamit Nobel | 38.0% |
| Expanded particles of vinylidene chloride/acrylonitrilelmethacrylate copolymer enclosing isobutane (Expancel 550 DE 20 from Nobel Casco) | 1.5% |
| Hydrophobic pyrogenous silica surface-modified with trimethylsiloxane (Aerosil R 972 from Degussa) | 1.0% |
| Silicone gel comprising a mixture of polydimethylsiloxane (0.06 Pa s)/crosslinked polydimethylsiloxane (75125) sold under the name KSG16 by Shin Etsu | 12.0% |
| Pigments | 4.5% |
| Talc | 11.0% |
| Fragrance | 0.3% |
| D,L-alpha-tocopherol (active agent) | 0.1% |
| cyclopentadimethylsiloxane | 21.6% |
| cyclohexadimethylsiloxane | 2.0% |
| Isostearyl neopentanoate | 8.0% |

The formulation of Example 2 was prepared according to the same process as that for Example 1.

EXAMPLE 3

Complexion Enhancer Giving an Apricot-like Color

| | |
|---|---|
| Hectorite modified with stearyldimethylammonium chloride in gel form sold under the name Miglyol Gel B from Dynamit Nobel | 35.0% |
| Expanded particles of vinylidene chloride/acrylonitrile/methacrylate copolymer enclosing isobutane (Expancel 550 DE 20 from Nobel Casco) | 1.5% |
| Hydrophobic pyrogenous silica surface-modified with trimethylsiloxane (Aerosil R 972 from Degussa) | 1.0% |
| Silicone gel comprising a mixture of polydimethylsiloxane (0.06 Pa s)/crosslinked polydimethylsiloxane (75/25) sold under the name KSG16 by Shin Etsu | 15.0% |
| Pigments | 4.5% |
| Talc | 8.0% |
| Fragrance | 0.3% |
| D,L-alpha-tocopherol (active agent) | 0.2% |
| Cyclopentadimethylsiloxane | 24.5% |
| Isostearyl neopentanoate | 10.0% |

The formulation of Example 3 was prepared according to the same process as that for Example 1.

EXAMPLE 4

Make-up Corrector

| | |
|---|---|
| Hectorite modified with stearyldimethylammonium chloride in gel form sold under the name Miglyol Gel B from Dynamit Nobel | 40.0% |
| Expanded particles of vinylidene chloride/acrylonitrile/methacrylate copolymer enclosing isobutane (Expancel 550 DE 20 from Nobel Casco) | 0.5% |
| Hydrophific pyrogenous silica (Aerosil 200 from Degussa) | 1.0% |
| Propyl parahydroxybenzoate | 0.2% |
| Pigments | 5.0% |

| Mica | 3.0% |
| --- | --- |
| Starch crosslinked with epichlorohydrin | 4.0% |
| Talc | 3.0% |
| Fragrance | 0.2% |
| Caprylic/capric acid triglycerides (60/40) | 14.1% |
| Cyclopentadimethyisiloxane | 29.0% |

The composition was prepared as follows:

The process was performed at room temperature. The pigments were dispersed in the volatile silicone oil. The gel based on modified hectorite was added with stirring. The pyrogenous silica was added and the mixture was homogenized. The fragrance, the active agents and the hollow expanded particles, which were impasted beforehand in the caprylic/capric acid triglycerides, were next incorporated. The talc and the crosslinked starch were next introduced. Finally, the dispersion was made fine by grinding.

The compositions of Examples 1 to 4 were stable after 1 hour of centrifugation at an acceleration of 900 G and were stable after 2 months of storage at room temperature, at 37° and 45° C. They remained smooth without release of oil.

They had a creamy texture characterized by:

1) their penetrometry: with a penetration of 20 to 40 g measured on a Stevens texture analyser with a mobile cone, travelling at a speed of 0.5 mm/s and for a depth of 5 mm.

(2) their viscosity: this was approximately between 10 and 21 Pa s after stirring for 10 minutes, measured with a Contrave mobile 4 machine.

We claim:

1. A composition in the form of an anhydrous gel comprising at least:
   (a) a fatty phase containing essentially no wax;
   (b) an organomodified clay;
   (c) expanded thermoplastic hollow particles of polymer or of copolymer formed from a monomer or from a mixture of monomers containing ethylenic unsaturation; and
   (d) a pyrogenous silica.

2. A composition according to claim 1, wherein said fatty phase represents from 60 to 85% by weight of the total weight of the composition.

3. A composition according to claim 1, wherein said fatty phase comprises at least one oil.

4. A composition according to claim 3, wherein said at least one oil is selected from mineral oils, animal oils and plant oils.

5. A composition according to claim 4, wherein said mineral oils, animal oils, and plant oils include liquid petrolatum, soya oil, sunflower oil, sesame oil, rapeseed oil, sweet almond oil, macadamia oil, blackcurrant seed oil, karite butter, the liquid fraction of karite butter, and perhydrosqualene.

6. A composition according to claim 3, wherein said at least one oil is selected from synthetic oils.

7. A composition according to claim 6, wherein said synthetic oils include fatty acid esters and fatty alcohols.

8. A composition according to claim 7, wherein said fatty acid esters and fatty alcohols include parleam, isostearyl neopentanoate, isopropyl myristate, isopropyl stearate, 2-ethylhexyl palmitate, isopropyl lanolate, isononyl isononanoate, isotridecyl isononanoate, octyl palmitate, oleyl alcohol, saturated fatty acid triglycerides of plant origin, and hydrogenated polyisobutene.

9. A composition according to claim 8, wherein said saturated fatty acid triglycerides of plant origin are caprylic/capric acid triglycerides.

10. A composition according to claim 3, wherein said at least one oil is selected from silicone oils.

11. A composition according to claim 10, wherein said silicone oils include cyclomethicone and polydimethylsiloxane oils.

12. A composition according to claim 11, wherein said cyclomethicone oils include cyclopentadimethylsiloxane and cyclohexadimethylsiloxane.

13. A composition according to claim 3, wherein said at least one oil is selected from phenylated silcone gums, hydroxylated silicone gums and fluoro oils.

14. A composition according to claim 3, wherein said at least one oil selected from mineral oils, animal oils, plant oils, and synthetic oils.

15. A composition according to claim 1, wherein said organomodified clay is a product of reaction of a hectorite or a montmorillonite with a quaternary ammonium salt.

16. A composition according to claim 15, wherein said quaternary ammonium salt is stearyldimethylbenzylammonium chloride or the quaternary ammonium chloride of formula:

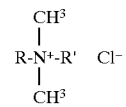

wherein R and R' independently represent a mixture of alkyl residues having from 14 to 20 carbon atoms derived from hydrogenated tallow.

17. A composition according to claim 1, wherein said organomodified clay is present in a concentration ranging from 0.5 to 6% by weight of active material relative to the total weight of the composition.

18. A composition according to claim 1, wherein said organomodified clay is in the form of a gel comprising:
   said organomodified clay; an oil of plant, mineral, animal, or synthetic origin; and a wetting agent.

19. A composition according to claim 18, wherein said wetting agent is propylene carbonate.

20. A composition according to claim 18, wherein said organomodified clay is in the form of a gel comprising:
   said organomodified clay; a mixture of capric and caprylic acid triglycerides; and propylene carbonate.

21. A composition according to claim 1, wherein said expanded thermoplastic hollow particles are particles of expanded polymer or copolymer formed from a monomer or a mixture of monomers containing ethylenic unsaturation.

22. A composition according to claim 21, wherein said monomer or mixture of monomers is selected from methacrylic and acrylic acid esters, vinylidene chloride, acrylonitrile, styrene and derivatives thereof; and butadiene.

23. A composition according to claim 21, wherein said thermoplastic hollow particles are dry or hydrated expanded copolymers of vinylidene cholride and acrylonitrile, or dry or hydrated expanded terpolymers of vinylidene chloride, acrylonitrile and methyl methacrylate.

24. A composition according to claim 21, wherein said expanded copolymer contains from 0% to 60% of vinylidene chloride or a vinylidene chloride residue, from 20% to 90% of acrylonitrile or an acrylonitrile residue, and from 0% to 50% of a (meth)acrylic or styrene monomer, the sum of the percentages (by weight) being equal to 100.

25. A composition according to claim 21, wherein said thermoplastic hollow particles have a particle size of from 1 to 100 μm.

26. A composition according to claim 21, wherein said thermoplastic hollow particles have a density ranging from 15 to 200 kg/cm³.

27. A composition according to claim 21, wherein said expanded thermoplastic hollow particles are present in concentrations ranging from 0.1 to 3% by weight relative to the total weight of the composition.

28. A composition according to claim 1, wherein said pyrogenous silica is present in concentrations ranging from 0.1 to 3% by weight relative to the total weight of the composition.

29. A composition according to claim 1, wherein said composition also contains a silicone gel comprising:

(a) a partially crosslinked polyorganosiloxane of three-dimensional structure chosen from:
  i) polyorganopolysiloxanes comprising units of $R_2SiO$ and $RSiO_{1.5}$ and optionally units of $R_3SiO_{0.5}$ and $SiO_2$ or $SiO_2$ in which the radicals R, independently of each other, denote a hydrogen, an alkyl, an aryl and an unsaturated aliphatic group and in which the weight ratio of the units of $R_2SiO$ to the units of $RSiO_{1.5}$ ranges from 1/1 to 30/1;
  ii) insoluble polyorganopolysiloxanes different from said polyorganopolysiloxanes i), said insoluble polyorganopolysiloxanes being swellable in silicone oil, and being obtained by addition of an organohydrogenopolysiloxane (1) and an organopolysiloxane (2) having unsaturated aliphatic groups, such that the amount of hydrogen or of unsaturated aliphatic groups in (1) and (2) respectively is from 1 to 20 mol % when the organopolysiloxane is non-cyclic and from 1 to 50 mol % when the organopolysiloxane is cyclic; and (b) a silicone oil of viscosity less than or equal to 0.5 Pa s; the partially crosslinked polyorganosiloxane/silicone oil weight ratio ranging from 5/95 to 30/70.

30. A composition according to claim 29, wherein said alkyl is methyl, ethyl or propyl; said aryl is phenyl or tolyl; and said unsaturated aliphatic group is vinyl.

31. A composition according to claim 29, wherein said silicone gel is included in a silicone oil of low viscosisty.

32. A composition according to claim 31, wherein said silicone oil is selected from a linear methylphenylpolysiloxane with a low degree of polymerization, a dimethylpolysiloxane with a low degree of polymerization, an octamethylcyclotetrasiloxane, a decamethylcyclopentasiloxane, and a mixture of said octamethylcyclotetrasiloxane and decamethylcyclopentasiloxane.

33. A composition according to claim 29, wherein said silicone gel comprises a linear polydimethylsiloxane of low viscosity and a partially crosslinked polydimethylsiloxane of three-dimensional structure.

34. A composition according to claim 29, wherein said partially crosslinked polyorganosiloxane is present in concentrations ranging up to about 8% by weight of active material relative to the total weight of the composition.

35. A composition according to claim 1, wherein said composition also contains at least one pigment.

36. A composition according to claim 1, wherein said composition also contains at least one agent in an amount effective to obtain a matte-effect.

37. A composition according to claim 35, wherein said pigment ranges up to 20% by weight relative to the total weight of the composition.

38. A composition according to claim 36, wherein said amount effective of said agent to obtain a matte-effect ranges from 2 to 15% by weight relative to the total weight of the composition.

39. A composition according to claim 1, wherein said composition also contains at least one adjuvant selected from cosmetic or dermatological active agents, antioxidants, bactericides, melanin, moisturizing agents, sunscreens, fragrances, preserving agents and fillers.

40. A method of making a make-up product or a care product for the skin or the face comprising the step of including the composition according to claim 1 as a base in said product.

41. A composition according to claim 1, wherein said fatty phase contains 1% or less of wax, relative to the total weight of the composition.

42. A composition according to claim 41, wherein said fatty phase contains 0.5% or less of wax, relative to the total weight of the composition.

43. A composition according to claim 42, wherein said fatty phase contains no wax.

44. A composition according to claim 14 wherein said synthetic oils include silicone oils, phenylated silicone gums, hydroxylated silicone gums and fluoro oils.

45. A composition according to claim 18 wherein said oil of synthetic origin is selected from silicone oil, phenylated silicone gum, hydroxylated silicone gum and fluoro oil.

* * * * *

UNITED STATES PATENT AND TRADEMARK OFFICE
CERTIFICATE OF CORRECTION

PATENT NO.: 5,846,550
DATED: December 8, 1998
INVENTOR(S): Martine PERRIN et al.

It is certified that an error appears in the above-identified patent and that said Letters Patent is hereby corrected as shown below:

In the *Attorney, Agent, or Firm* section, please change "Henders" to --Henderson--.

Signed and Sealed this

Twenty-third Day of March, 1999

*Attest:*

Q. TODD DICKINSON

*Attesting Officer*     *Acting Commissioner of Patents and Trademarks*